US012582841B2

(12) United States Patent
Yamada et al.

(10) Patent No.: US 12,582,841 B2
(45) Date of Patent: Mar. 24, 2026

(54) WORKFLOW MANAGEMENT SYSTEM, RADIOTHERAPY SYSTEM, AND WORKFLOW MANAGEMENT METHOD

(71) Applicant: Hitachi High-Tech Corporation, Tokyo (JP)

(72) Inventors: Takahiro Yamada, Tokyo (JP); Yusuke Fujii, Tokyo (JP); Toru Umekawa, Tokyo (JP); Yoshihiko Nagamine, Tokyo (JP); Takao Kidani, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 279 days.

(21) Appl. No.: 18/027,466

(22) PCT Filed: Aug. 10, 2021

(86) PCT No.: PCT/JP2021/029542
§ 371 (c)(1),
(2) Date: Mar. 21, 2023

(87) PCT Pub. No.: WO2022/158012
PCT Pub. Date: Jul. 28, 2022

(65) Prior Publication Data
US 2024/0082603 A1      Mar. 14, 2024

(30) Foreign Application Priority Data

Jan. 25, 2021      (JP) ................................. 2021-009502

(51) Int. Cl.
A61N 5/10          (2006.01)
G16H 20/40          (2018.01)
(52) U.S. Cl.
CPC ........... A61N 5/1038 (2013.01); A61N 5/103 (2013.01); A61N 5/1037 (2013.01);
(Continued)

(58) Field of Classification Search
CPC ........ A61N 5/10; A61N 5/103; A61N 5/1031; A61N 5/1037; A61N 5/1038;
(Continued)

(56) References Cited

U.S. PATENT DOCUMENTS 5,651,043 A * 7/1997 Tsuyuki ............... A61N 5/1042
378/65
6,990,175 B2 * 1/2006 Nakashima ............ A61B 6/032
378/92

(Continued)

FOREIGN PATENT DOCUMENTS

EP        2 654 574 B1      5/2017
JP        2012-506734 A      3/2012

(Continued)

OTHER PUBLICATIONS

Extended European Search Report received in corresponding European Application No. 21921117.4 dated Nov. 15, 2024.

(Continued)

*Primary Examiner* — Allen C. Ho
(74) *Attorney, Agent, or Firm* — MATTINGLY & MALUR, PC

(57) ABSTRACT
A time required for online adaptive treatment is reduced with a workflow management system that executes a plurality of processes for radiotherapy according to a predetermined workflow. The plurality of processes include at least a first process and a second process, and the workflow management system executes the following modules, in parallel, including a first module that is included in the first process, displays a result of a first calculation based on a patient image captured during treatment by an imaging apparatus that captures a predetermined region of a patient, and requests an input from an operator; and a second module
(Continued)

that is included in the second process, and executes a second calculation based on the patient image during the treatment.

19 Claims, 6 Drawing Sheets

(52) U.S. Cl.
CPC ......... *A61N 5/1042* (2013.01); *A61N 5/1048* (2013.01); *A61N 5/1049* (2013.01); *A61N 5/1064* (2013.01); *A61N 5/1065* (2013.01); *A61N 5/1067* (2013.01); *A61N 5/1069* (2013.01); *A61N 5/107* (2013.01); *A61N 5/1081* (2013.01); *A61N 2005/1061* (2013.01); *A61N 2005/1074* (2013.01); *G16H 20/40* (2018.01)

(58) Field of Classification Search
CPC .. A61N 5/1042; A61N 5/1045; A61N 5/1047; A61N 5/1048; A61N 5/1049; A61N 2005/1052; A61N 2005/1061; A61N 5/1064; A61N 5/1065; A61N 5/1069; A61N 5/107; A61N 5/1071; A61N 2005/1072; A61N 2005/1074; A61N 5/1077; A61N 5/1081; A61N 5/1082; A61N 5/1039; A61B 5/1067
USPC .......................................................... 378/65
See application file for complete search history.

(56) References Cited

U.S. PATENT DOCUMENTS

| | | | | |
|---|---|---|---|---|
| 7,345,274 B2 * | 3/2008 | Nilsson | ................ | A61N 5/1048 378/207 |
| 7,453,983 B2 * | 11/2008 | Schildkraut | .......... | A61N 5/1049 378/65 |
| 7,574,251 B2 * | 8/2009 | Lu | ........................ | A61N 5/1031 600/411 |
| 7,611,452 B2 * | 11/2009 | Allison | .................. | A61N 5/103 600/1 |
| 7,623,679 B2 * | 11/2009 | West | .................... | A61N 5/1031 382/128 |
| 7,713,205 B2 * | 5/2010 | Fu | ........................ | A61N 5/1049 600/443 |
| 7,817,778 B2 * | 10/2010 | Nord | .................... | A61N 5/1047 378/65 |
| 7,894,649 B2 * | 2/2011 | Fu | ........................ | A61N 5/1049 378/65 |
| 8,077,936 B2 * | 12/2011 | Wang | .................... | A61N 5/103 382/128 |
| 8,086,004 B2 * | 12/2011 | Kuduvalli | ............ | A61N 5/1075 382/128 |
| 8,175,892 B2 * | 5/2012 | Kapoor | ................ | A61N 5/1081 378/65 |
| 8,232,535 B2 * | 7/2012 | Olivera | ................ | A61N 5/1042 250/493.1 |
| 8,295,435 B2 * | 10/2012 | Wang | ................... | A61N 5/1082 378/65 |
| 8,306,185 B2 * | 11/2012 | Bal | ........................ | G16H 20/40 378/65 |
| 8,406,844 B2 * | 3/2013 | Ruchala | ................ | A61N 5/103 378/65 |
| 8,467,497 B2 * | 6/2013 | Lu | ........................ | A61N 5/1049 378/65 |
| 8,509,383 B2 * | 8/2013 | Lu | ........................ | A61N 5/1049 378/65 |
| 8,559,596 B2 * | 10/2013 | Thomson | ............. | A61B 6/4071 378/65 |
| 8,767,917 B2 * | 7/2014 | Ruchala | ............... | A61N 5/1049 378/65 |
| 8,804,901 B2 * | 8/2014 | Maurer, Jr. | ......... | A61N 5/1049 378/21 |
| 8,812,077 B2 * | 8/2014 | Dempsey | ............. | A61N 5/1049 600/410 |
| 8,874,187 B2 * | 10/2014 | Thomson | ............. | A61N 5/1039 378/65 |
| 8,992,405 B2 * | 3/2015 | Chebrolu | ............. | A61N 5/1049 378/65 |
| 9,020,234 B2 * | 4/2015 | Netsch | ..................... | G06T 7/12 382/131 |
| 9,586,059 B2 * | 3/2017 | Herron | ................. | A61N 5/1049 |
| 10,029,121 B2 * | 7/2018 | Li | ......................... | A61N 5/1037 |
| 10,143,431 B2 * | 12/2018 | Hirai | ................... | A61N 5/1049 |
| 10,152,951 B2 * | 12/2018 | Waschbuesch | .......... | G06T 5/92 |
| 10,279,196 B2 * | 5/2019 | West | .................... | A61N 5/1031 |
| 10,512,507 B2 * | 12/2019 | Kumar | ................... | A61B 34/10 |
| 10,537,749 B2 * | 1/2020 | Isola | .................... | A61N 5/1045 |
| 10,799,716 B2 * | 10/2020 | Morgas | .................. | A61N 5/103 |
| 10,866,832 B2 * | 12/2020 | Ohba | ................... | G06F 9/4881 |
| 11,173,323 B2 * | 11/2021 | Munbodh | ........... | A61N 5/1031 |
| 11,173,324 B2 * | 11/2021 | Paysan | ................. | A61N 5/1045 |
| 11,278,737 B2 * | 3/2022 | Peltola | ................ | A61N 5/1031 |
| 11,577,095 B2 * | 2/2023 | Vojan | .................. | A61N 5/1039 |
| 11,604,564 B2 * | 3/2023 | Vojan | .................... | G16H 30/20 |
| 11,607,563 B2 * | 3/2023 | Vojan | .................. | A61N 5/1081 |
| 11,638,840 B2 * | 5/2023 | Vojan | .................. | A61N 5/1049 378/65 |
| 11,654,303 B2 * | 5/2023 | Vojan | .................. | A61N 5/1064 378/65 |
| 11,660,473 B2 * | 5/2023 | Vojan | .................. | A61N 5/1081 378/205 |
| 11,679,276 B2 * | 6/2023 | Novosad | ................ | G06N 20/10 378/65 |
| 11,712,587 B2 * | 8/2023 | Vojan | .................. | A61N 5/1081 378/65 |
| 11,759,656 B2 * | 9/2023 | Vojan | .................. | A61N 5/1081 378/65 |
| 11,786,756 B2 * | 10/2023 | Vojan | .................. | A61N 5/1037 378/65 |
| 11,786,757 B2 * | 10/2023 | Vojan | .................... | G16H 40/20 378/205 |
| 11,817,210 B2 * | 11/2023 | Vojan | .................... | G16H 20/40 |
| 11,844,962 B2 * | 12/2023 | Vojan | .................... | G16H 40/20 |
| 12,011,612 B2 * | 6/2024 | Zhou | ..................... | A61N 5/103 |
| 2005/0151071 A1 | 7/2005 | Nilsson | | |
| 2009/0252291 A1 | 10/2009 | Lu et al. | | |
| 2012/0323599 A1 | 12/2012 | Bal et al. | | |
| 2016/0175052 A1 | 6/2016 | Kumar et al. | | |
| 2019/0213040 A1 | 7/2019 | Ohba | | |
| 2020/0121951 A1 | 4/2020 | Morgas et al. | | |

FOREIGN PATENT DOCUMENTS

| | | | |
|---|---|---|---|
| JP | 2013-521843 A | 6/2013 |
| JP | 2019-121240 A | 7/2019 |

OTHER PUBLICATIONS

International Search Report of PCT/JP2021/029542 dated Oct. 5, 2021.
Japanese Office Action received in corresponding Japanese Application No. 2021-009502 dated Jul. 2, 2024.

* cited by examiner

*FIG. 3*

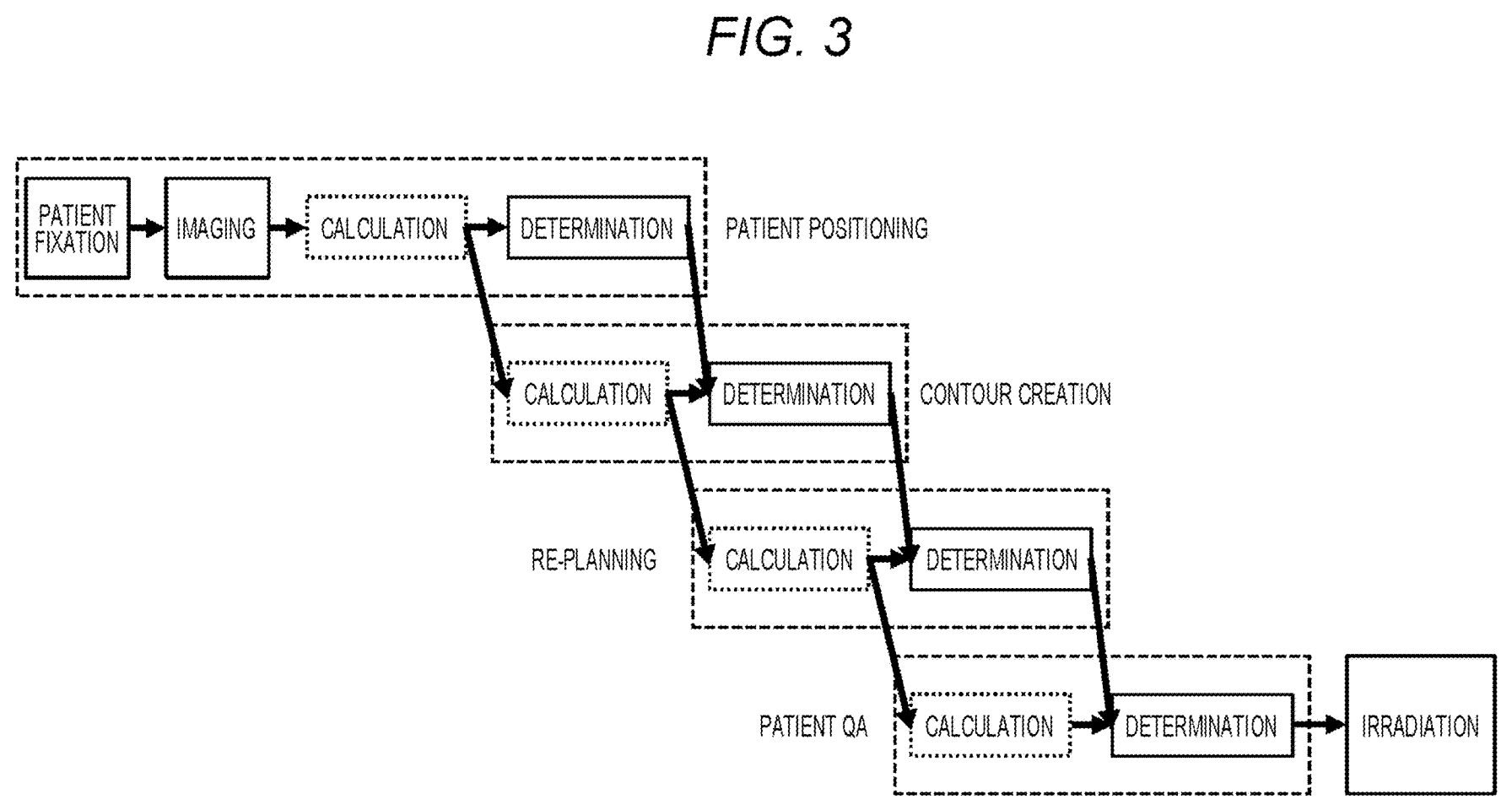

PATIENT FIXATION → IMAGING → CALCULATION

PATIENT POSITIONING
CALCULATION → DETERMINATION

CONTOUR CREATION
DETERMINATION → DETERMINATION

RE-PLANNING
CALCULATION

PATIENT QA
CALCULATION → DETERMINATION → IRRADIATION

WORKFLOW MANAGEMENT SYSTEM, RADIOTHERAPY SYSTEM, AND WORKFLOW MANAGEMENT METHOD

TECHNICAL FIELD

The present invention relates to a workflow management system, a radiotherapy system, and a workflow management method.

BACKGROUND ART

The present invention relates to the workflow management system applied to the radiotherapy system that irradiates and treats an affected area such as a tumor with radiation such as a particle beam, the radiotherapy system, and the workflow management method.

A method for irradiating a patient with cancer or the like with radiation such as a particle beam or an X-ray is known. Examples of the particle beam include a proton beam and a carbon ion beam. The radiotherapy system used for irradiation forms dose distribution suitable for a shape of a target such as a tumor in a body of the patient fixed to a patient bed called a couch.

Conditions in the body of the patient changes every day, such as a change in the shape of the target and a change in a gas pocket of an intestinal tract. In order to improve irradiation accuracy, adaptive treatment in which treatment planning is recreated according to the conditions in the body of the patient on a treatment day has begun to spread. In particular, treatment in which the treatment planning is recreated while the patient is fixed to the couch on the treatment day is called online adaptive treatment.

As an example of a workflow of online adaptive radiotherapy for recreating the treatment planning on site according to the conditions in the body of the patient on the treatment day, PTL 1 describes a workflow of online adaptive radiotherapy characterized by automatically executing steps of obtaining a command representing treatment planning, generating a patient model stepwise using the command, generating first and second treatment planning, and selecting treatment planning.

CITATION LIST

Patent Literature

PTL 1: US 2020/0121951 A

SUMMARY OF INVENTION

Technical Problem

PTL 1 described above describes an automatic workflow of the online adaptive treatment. In this workflow, patient fixation, imaging, contour creation, treatment planning creation and selection, and irradiation are sequentially executed. In the conventional treatment, the treatment is executed in three steps of patient fixation, imaging, and irradiation, but in the online adaptive treatment, there is a possibility that the treatment time increases due to an increase in implementation matters.

The present invention has been made in view of the above problems, and an object of the present invention is to provide a workflow management system capable of executing the online adaptive treatment in a short time, a radiotherapy system, and a workflow management method.

Solution to Problem

In order to solve the above problems, for example, the configuration described in the claims is adopted. That is, the present invention is a workflow management system that executes a plurality of processes executed to execute radiotherapy according to a predetermined workflow, in which the plurality of processes includes at least a first process and a second process, and the workflow management system executes the following modules (a) and (b) in parallel:

(a) a first module that is included in the first process, displays a result of a first calculation based on a patient image captured during treatment by an imaging apparatus that captures a predetermined region of a patient, and requests an input from an operator;

(b) a second module that is included in the second process, and executes a second calculation based on the patient image during the treatment.

Advantageous Effects of Invention

According to the present invention, a time required for the online adaptive treatment can be reduced.

BRIEF DESCRIPTION OF DRAWINGS

FIG. 3 is a basic conceptual diagram of workflow management in the workflow manager according to the embodiment.

DESCRIPTION OF EMBODIMENTS

Figure 1:
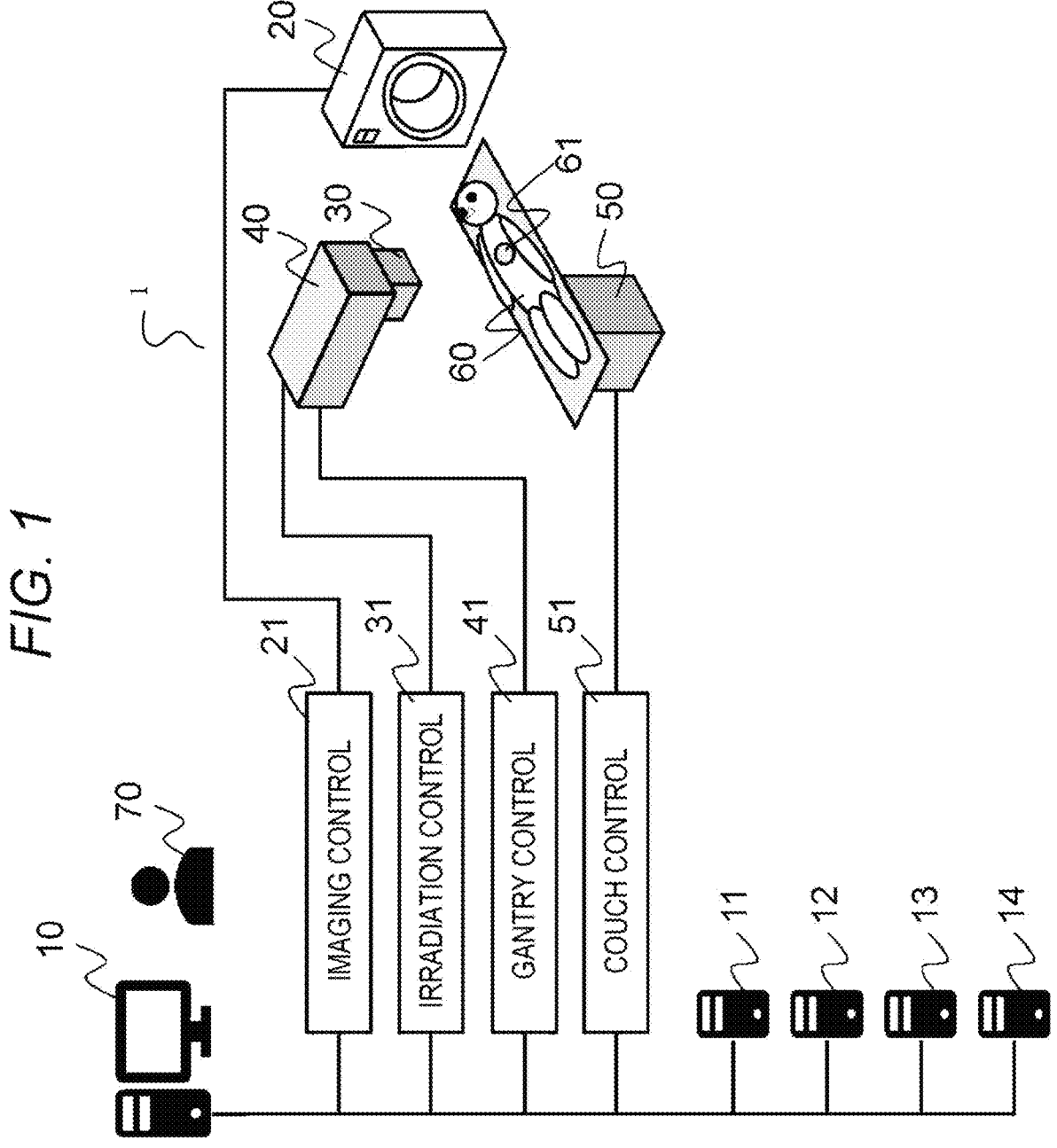
FIG. 1 is an overall configuration diagram of a radiotherapy system including a workflow manager according to an embodiment.

Hereinafter, embodiments of the present invention will be described with reference to the drawings. The following description and drawings are examples for describing the present invention, and are omitted and simplified as appropriate for the sake of clarity of description. The present invention can be carried out in various other forms. Unless otherwise specified, each component may be singular or plural.

Note that in the drawings for describing the embodiments, portions having the same functions are denoted by the same reference numerals, and repeated description thereof will be omitted.

Positions, sizes, shapes, ranges, and the like of the components illustrated in the drawings may not represent actual positions, sizes, shapes, ranges, and the like in order to facilitate understanding of the invention. Therefore, the present invention is not necessarily limited to the positions, sizes, shapes, ranges, and the like disclosed in the drawings.

In a case where there is a plurality of components having the same or similar functions, the same reference numerals may be attached with different subscripts for description. However, in a case where it is not necessary to distinguish the plurality of components, the description may be made while omitting the subscript.

As illustrated in FIG. 1, a radiotherapy system 1 according to the embodiment includes a workflow manager 10, a patient positioning system 11, a contour creation system 12, a re-planning system 13, a patient quality assurance (QA) system 14, an imaging apparatus 20, an imaging control system 21, an irradiation nozzle 30, an irradiation control system 31, a rotating gantry 40, a gantry control system 41, a couch 50, and a couch control system 51.

A bed on which a patient 60 is placed is referred to as the couch 50. The couch 50 can move in directions of three orthogonal axes on the basis of an instruction from the couch control system 51, and can further rotate about the respective axes. These movements and rotations can move a position of a target 61 to a desired position.

An imaging apparatus 20 measures a three-dimensional image of the patient 60 fixed to the couch 50 and the target 61 on the basis of an instruction from the imaging control system 21. The three-dimensional image is a CT image, a cone beam CT image, or an MRI image.

The irradiation nozzle 30 generates radiation used for treatment on the basis of an instruction from the irradiation control system 31. Specifically, desired dose distribution is formed for the target 61 by controlling energy, an irradiation position, and an irradiation dose of the radiation. A part of the irradiation nozzle 30 is installed in the rotating gantry 40 and can rotate together with the rotating gantry 40. The rotating gantry 40 is moved to a desired angle on the basis of an instruction from the gantry control system 41. By changing the angle of the rotating gantry 40, radiation can be emitted from a desired angle.

The patient positioning system 11 calculates a position correction amount of the patient 60 with respect to the irradiation nozzle 30 on the basis of a reference image generated in advance and the three-dimensional image measured by the imaging apparatus 20. An operator 70 checks a calculation result and determines the position correction amount. On the basis of the determined position correction amount, an installation position of the couch 50 is calculated and set in the couch control system 51.

The contour creation system 12 generates a synthetic CT image used for re-planning on the basis of the reference image generated in advance and the three-dimensional image measured by the imaging apparatus 20. Further, regions of the target and normal tissue are specified on the synthetic CT image, and contour data thereof is created. The operator 70 checks the calculation result, corrects the calculation result as necessary, and then approves the synthetic CT image and the contour data.

The re-planning system 13 optimizes an irradiation parameter of the radiation on the basis of the synthetic CT image and the contour data to create a day plan. Further, an original treatment planning generated in advance (hereinafter referred to as an original plan) and dose distribution of the day plan are compared and displayed. The operator 70 selects treatment planning to be used for treatment on the day.

The patient QA system 14 verifies the day plan, and the operator checks and approves a verification result.

The workflow manager 10 is connected to the imaging control system 21, the irradiation control system 31, the gantry control system 41, the couch control system 51, the patient positioning system 11, the contour creation system 12, the re-planning system 13, and the patient QA system 14, and monitors and manages a progress status of a treatment workflow.

Here, the workflow management system of the present embodiment includes at least the workflow manager 10, and further includes the patient positioning system 11, the contour creation system 12, the re-planning system 13, and the patient QA system 14.

Figure 2:
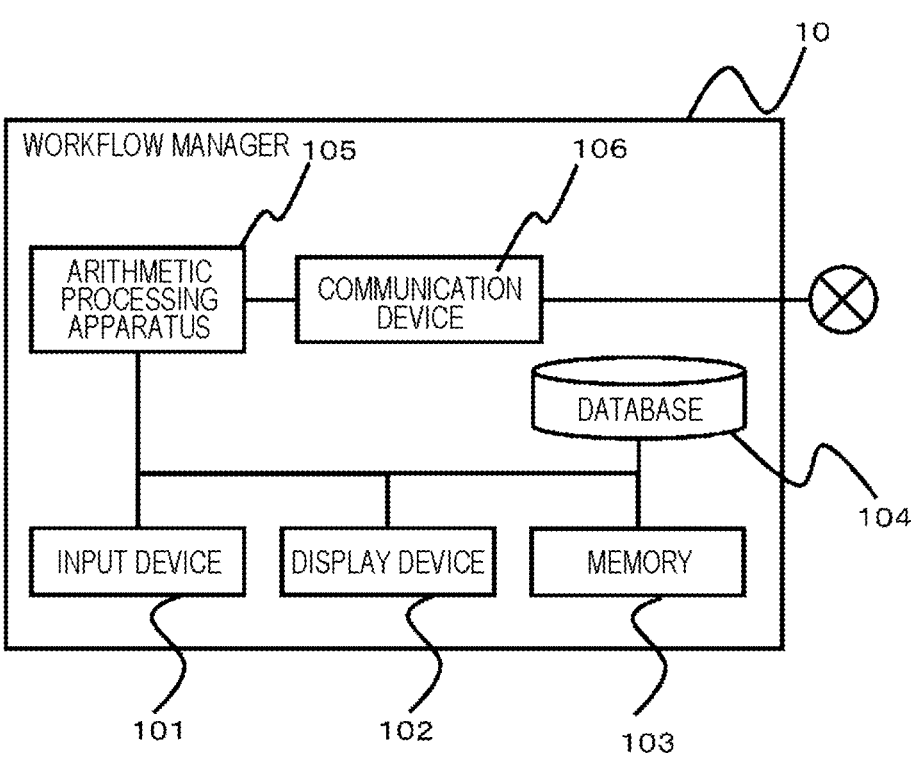
FIG. 2 is a block diagram illustrating the workflow manager according to the embodiment.

FIG. 2 is a schematic configuration diagram illustrating the workflow manager 10 according to the embodiment.

As illustrated in FIG. 2, the workflow manager 10 includes an input device 101 for inputting various parameters and the like, a display device 102, a memory (storage medium) 103, a database (storage medium) 104, an arithmetic processing apparatus 105 (a control apparatus that is an arithmetic element) that creates the workflow and monitors and manages the progress status of the workflow, and a communication device 106.

The workflow manager 10 includes a device capable of conducting various types of information processing, for example, an information processing apparatus such as a computer.

The arithmetic element is, for example, a central processing unit (CPU), a graphic processing unit (GPU), a field-programmable gate array (FPGA), or the like. The storage medium includes, for example, a magnetic storage medium such as a hard disk drive (HDD), a semiconductor storage medium such as a random access memory (RAM), a read only memory (ROM), and a solid state drive (SSD), and the like. Further, a combination of an optical disk such as a digital versatile disk (DVD) and an optical disk drive is also used as the storage medium. In addition, a known storage medium such as a magnetic tape medium is also used as the storage medium.

A program such as firmware is stored in the storage medium. When operation of the workflow manager 10 is started (for example, when a power is turned on), the program such as firmware is read from the storage medium and executed, and an overall control of the workflow manager 10 is performed. Further, in addition to the program, the storage medium stores data and the like necessary for each processing of the workflow manager 10.

Alternatively, some of components constituting the workflow manager 10 may be connected to each other via a local area network (LAN) or may be connected to each other via a wide area network (WAN) such as the Internet.

Further, although not illustrated, various apparatuses and systems constituting the radiotherapy system 1, such as the patient positioning system 11 also include the information processing apparatus such as the computer.

FIG. 3 illustrates a basic concept of workflow management performed by the workflow manager 10 or the like of the present embodiment.

The workflow manager 10, the patient positioning system 11, and the like execute each process of patient positioning, contour creation, re-planning, patient QA, and irradiation, similarly to a general online adaptive treatment. A feature of the radiotherapy system of the present embodiment is to start calculation of a next process during execution of a step of requesting determination and operation by the operator 70, such as checking and correction of the calculation result, in each process. When there is no correction of the calculation result by the operator 70, previously-started calculation is continued. When there is correction of the calculation result by the operator 70, the previously-started calculation is stopped, and the calculation of the next process is started by reflecting the corrected calculation result.

The workflow manager 10 manages steps executed in each process as modules divided for each element.

Figure 4:
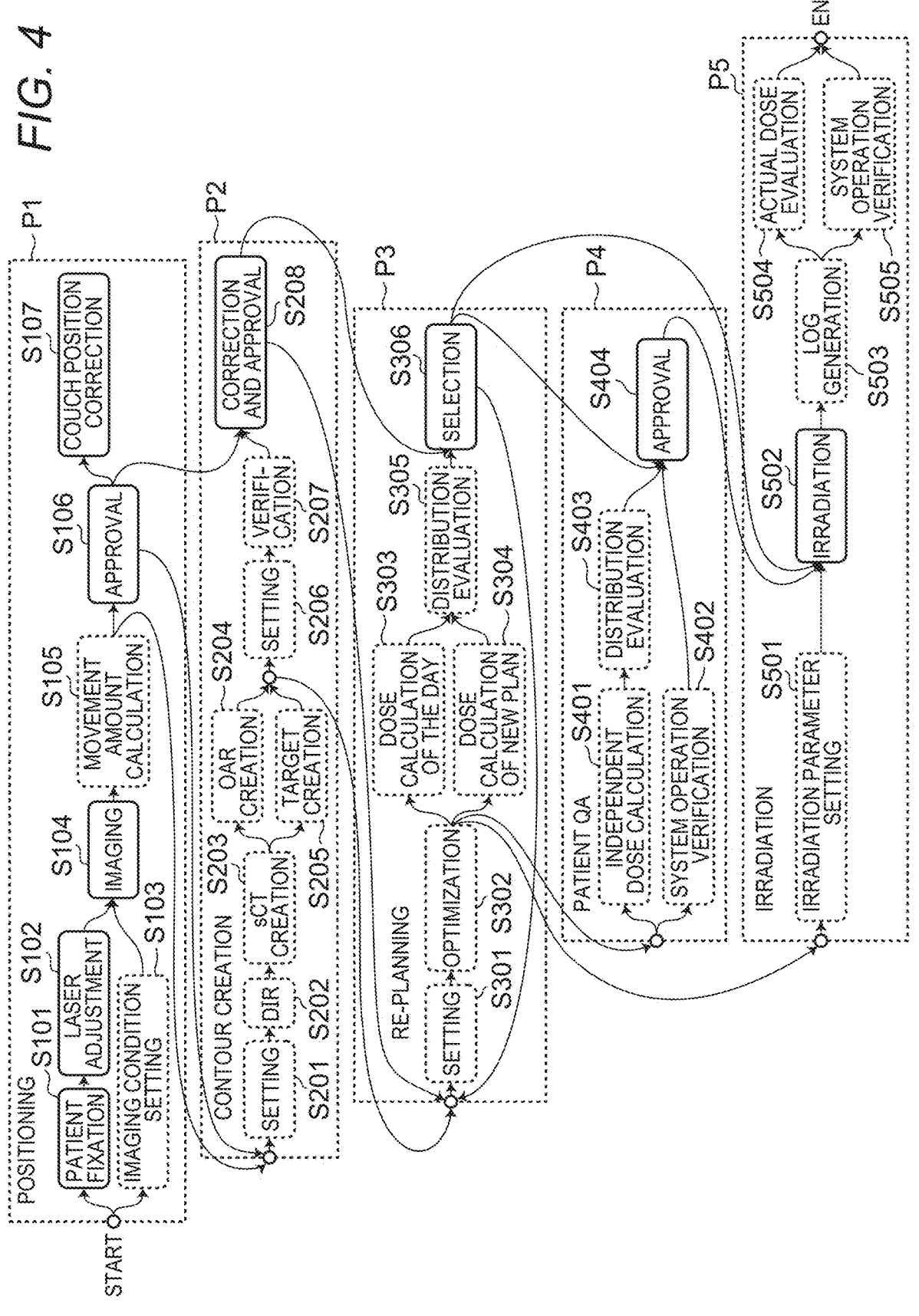
FIG. 4 is a conceptual diagram of the workflow management in the workflow manager according to the embodiment.

FIG. 4 illustrates an example of a module-managed workflow. In the entire workflow, a range surrounded by a broken line indicates each process. Among the processes, automatically implemented modules are indicated by dotted lines, and modules that need to be implemented (determined and operated) by the operator 70 (that is, manually implemented modules) are indicated by solid lines. The modules that need to be implemented by the operator 70 are implemented after determination and operation by the operator 70.

Before starting the treatment, the workflow manager 10 holds the CT image, the contour data, the irradiation parameter, a dose distribution index, and a clinical goal as information of the original plan created in a treatment preparation period.

The workflow includes a positioning process P1, a contour creation process P2, a re-planning process P3, a patient QA process P4, and an irradiation process P5. Software modules that respectively execute steps of the positioning process P1, the contour creation process P2, the re-planning process P3, and the patient QA process P4 are respectively held by the patient positioning system 11, the contour creation system 12, the re-planning system 13, and the patient QA system 14, and are respectively executed by the patient positioning system 11 and the like.

The workflow manager 10 monitors an execution status of each software module executed by the patient positioning system 11 and the like, and receives an execution result (a calculation result) and an execution end notification of the software module as necessary. Once a step is completed, the workflow manager 10 identifies a next step in accordance with the workflow and instructs the software module of the patient positioning system 11 or the like to begin this step.

Hereinafter, a workflow management method will be described for each process.

In the positioning process P1, in step S101, the operator 70 fixes the patient 60 to the couch 50. Further, in step S102, the operator 70 adjusts the position of the couch 50 in order to roughly position the patient 60 with respect to the irradiation nozzle 30 with reference to a laser marker (not illustrated).

In parallel with steps S101 and S102, in S103, imaging conditions of the imaging apparatus 20 is set by the workflow manager 10. The imaging conditions are set on the basis of information on the patient 60, a treatment site, and a previous treatment date.

In step S104, three-dimensional images on the day of the patient 60 and the target 61 are measured. In step S105, the position correction amount of the patient 60 with respect to the irradiation nozzle 30 is calculated on the basis of the three-dimensional image on the day using the CT image of the original plan as the reference image. When step S105 is completed, step S106 and S201 of the contour creation process P2 are executed.

In step S106, approval of the calculation result by the operator 70 is requested. The operator 70 checks the calculation result and corrects the position correction amount of the patient 60 as necessary. When the position correction amount is corrected by the operator 70, the calculation being executed in the contour creation process P2 is discarded, and the process is executed again from step S201 on the basis of the corrected position correction amount. When the position correction amount is approved in step S106, the position of the couch 50 is corrected in step S107. In addition, the workflow manager 10 inputs information indicating that the positioning process P1 has been completed to the software module that executes step S208.

In the contour creation process P2, first, in step S201, calculation conditions for deformable image registration (DIR) are set on the basis of the CT image of the original plan and information of the treatment site. In step S202, a deformable vector field (DVF) is calculated by deforming the CT image of the original plan by deformable image registration using a CT three-dimensional image on the day as the reference image on the basis of the set calculation conditions. In step S203, a synthetic CT (sCT) image in which pixel values of the three-dimensional image on the day are replaced with pixel values of the CT image of the original plan is generated using the calculated DVF.

When step S203 is completed, steps 204 and S205 are executed. In step S204, a contour of the normal tissue is calculated on the basis of the synthetic CT image and the DVF. In step S205, a contour of the target is calculated on the basis of the synthetic CT image and the DVF. Step S204 and step S205 may be executed simultaneously or sequentially. In a case of being sequentially executed, subsequent steps may be executed using a calculation result previously executed.

When steps S204 and S205 are completed, step S206 and S301 of the re-planning process P3 are executed. In step S206, calculation conditions of contour verification is set on the basis of the CT image of the original plan, the contour data, and the information of the treatment site. In step S207, calculation for verifying the contour data generated in steps S204 and S205 is executed on the basis of the CT image of the original plan, the contour data, and the information of the treatment site.

In step S208, the synthetic CT image, the contour data, and a contour verification result are displayed, and approval of the contour by the operator 70 is requested. The operator 70 checks the calculation result and corrects the contours of the normal tissue and the target as necessary. When the contour is corrected by the operator 70, the calculation being executed in the re-planning process P3 is discarded, and the process is executed again from step S301 on the basis of the corrected contour. When the contour is approved in step S208, the workflow manager 10 inputs information indicating that the contour creation process P2 has been completed to the software module that executes step S306. Note that step S208 is not executed unless the information indicating that the positioning process P1 has been completed is input.

In the re-planning process P3, first, in step S301, conditions for optimizing the irradiation parameter are set on the basis of the irradiation parameter of the original plan, the dose distribution index, and the clinical goal. Here, the conditions are a dose distribution shape, a dose volume histogram (DVH) index of the target and organ at risk (OAR), a weighting factor of optimization, and the like. In step S302, the irradiation parameter is optimized on the basis of the synthetic CT image and the contour data to create the day plan.

When step S302 is completed, step S303, step S304, steps S401 and S402 of the patient QA process P4, and step S501 of the irradiation process P5 are executed.

In step S303, dose distribution in a case where the irradiation is conducted as the original treatment planning is calculated on the basis of the irradiation parameter of the original plan and the synthetic CT image. In step S304, the dose distribution of the day plan is calculated on the basis of the irradiation parameter of the day plan and the synthetic CT image. In step S305, for two dose distributions calculated in steps S303 and S304, dose distribution indexes such as a DVH index, a homogeneity index (HI), and a conformity index (CI) of the target and the OAR are calculated on the basis of the contour data of the original plan and the day plan, and an achievement status of the clinical goal is displayed.

In step S306, an evaluation index calculated in step S305 is displayed, and selection of the treatment planning by the operator 70 is requested. The operator 70 checks the evaluation index and selects treatment planning to be used for treatment on that day from the original plan and the day plan. When the original plan is selected, the calculation being executed in the patient QA process P4 is discarded, and step S501 of the irradiation process P5 is executed again. Further, the workflow manager 10 inputs information indicating that the original plan has been selected to the software module that executes step S502. Furthermore, when the day plan is selected, the workflow manager 10 inputs information indicating that the re-planning process P3 has been completed to the software module that executes step S404. When it is determined that modification is necessary for the day plan, the process returns to step S301, and the re-planning process P3 is conducted again. Note that step S306 is not executed unless the information indicating that the contour creation process P2 has been completed is input.

In the patient QA process P4, first, steps S401 and S402 are executed. In step S401, on the basis of the synthetic CT image and the irradiation parameter of the day plan, the dose distribution of the day plan is calculated using a dose calculation algorithm different from that in step S303. In step S402, it is verified that the radiotherapy system 1 operates correctly during irradiation using the irradiation parameter of the day plan.

In step S403, on the basis of the dose distribution calculated in step S401 and the contour data of the day plan, the dose distribution indexes such as the DVH index, the HI, and the CI of the target and the OAR are calculated, and achievement status of the clinical goal is displayed. In addition, a degree of coincidence between the dose distributions calculated in steps S304 and S401 is evaluated by gamma analysis.

In step S404, the evaluation result calculated in step S403 and the verification result in step S402 are displayed, and checking of the result by the operator 70 is requested. When the operator 70 approves the result, the workflow manager 10 inputs information indicating that the patient QA process P4 has been completed to the software module that executes step S502. When the operator 70 does not approve the result, a request is made to choose between re-executing the treatment process or stopping the treatment. When re-execution of the treatment process is selected, selection of a re-execution step is requested. Note that step S404 is not executed unless the information indicating that the re-planning process P3 has been completed is input.

In the irradiation process P5, first, the irradiation parameter is set in each control system in step S501.

Next, if the information indicating that the original plan has been selected or the information indicating that the patient QA process P4 has been completed is input from the workflow manager 10, step S502 is executed. In step S502, the operator 70 is requested to permit execution of the irradiation, and if permitted, the irradiation is started. When the treatment planning includes a plurality of irradiation fields, the position of the couch 50 and the angle of the rotating gantry 40 are sequentially corrected to conduct the irradiation.

When the irradiation is completed, irradiation log data is generated in step S503. The irradiation log data includes data of the irradiation position and the irradiation dose of the radiation. When step S503 is completed, steps S504 and S505 are executed. In step S504, an actual dose distribution is calculated on the basis of the irradiation log data and the synthetic CT image. Further, the dose distribution index of the actual dose distribution is calculated using the contour data of the day plan.

In step S505, operation of the radiotherapy system 1 during irradiation is verified on the basis of the irradiation log data and the irradiation parameter of the day plan. When steps S504 and S505 are completed, the treatment is completed.

Next, a method of creating the workflow will be described. The workflow is created for each treatment site or treatment protocol and registered in the workflow manager 10. The workflow to be used during treatment is selected from workflows registered for each treatment planning.

Figure 5:
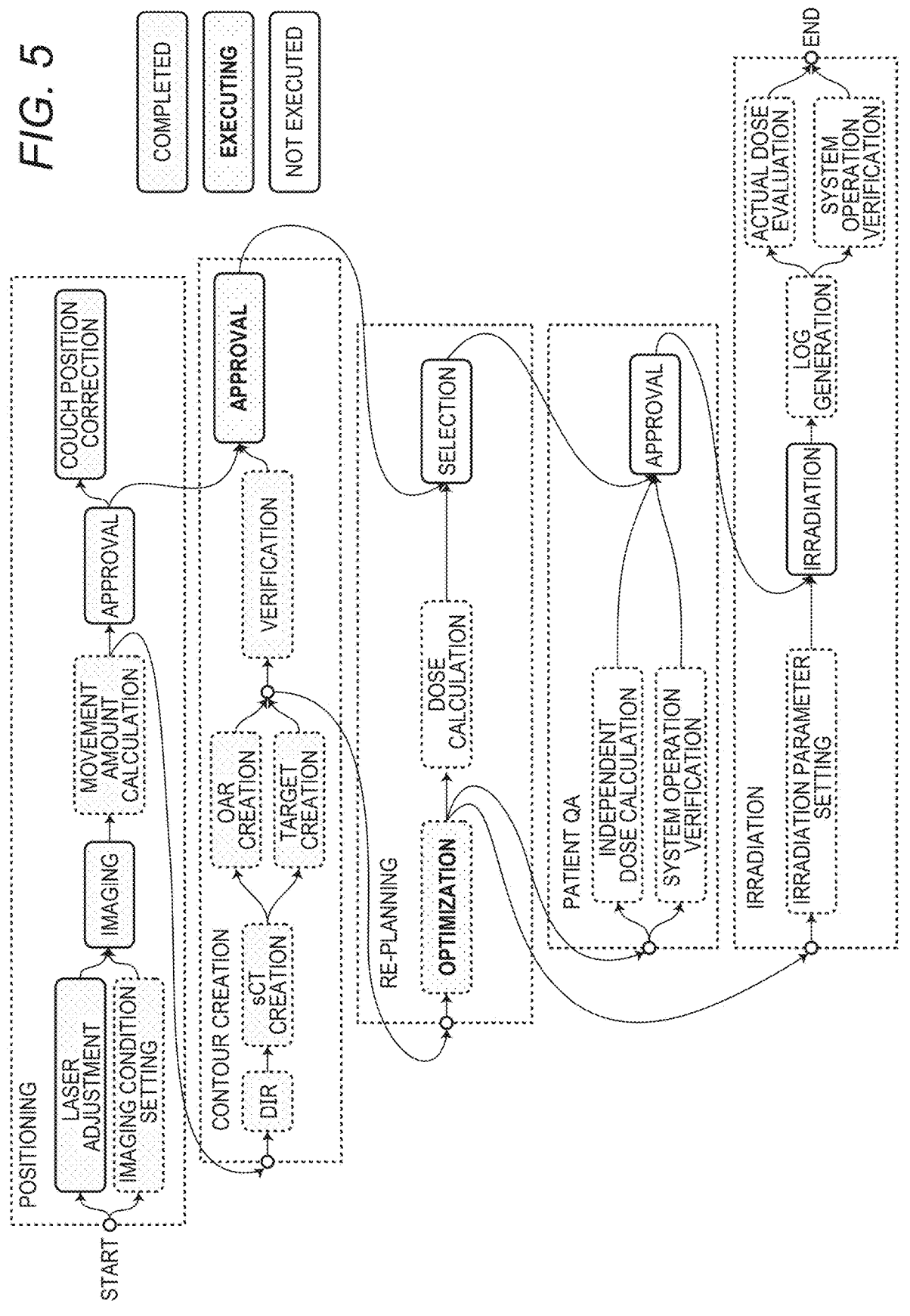
FIG. 5 is a diagram illustrating a display portion that displays a progress status of a workflow in the workflow manager according to the embodiment.

FIG. 5 illustrates a screen display of the workflow manager 10 during treatment. Three states of completed, executing, and not executed are displayed for each step of the workflow.

Figure 6:
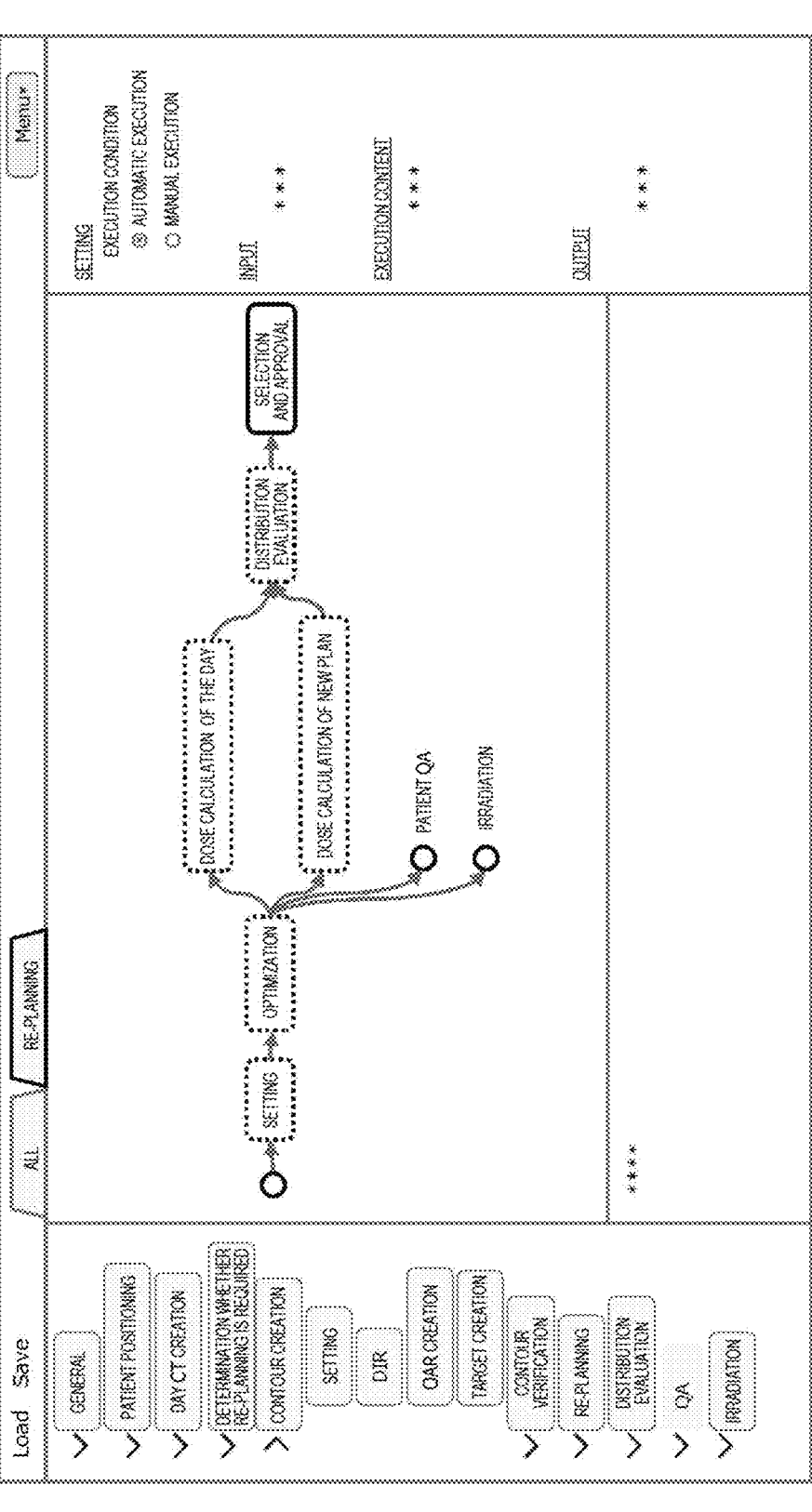
FIG. 6 is a diagram illustrating a display portion at the time of creating the workflow by the workflow manager according to the embodiment.

FIG. 6 illustrates the screen display of the workflow manager 10 at the time of creating the workflow. A left region is a part for selecting a registered module. An upper central region is apart that builds the workflow, and builds a progress of the steps in the process by connecting the modules. A lower central region is a part for displaying an error message or the like.

The right region is a region for setting each module, and sets an execution condition, an input/output content, and an execution content. In the execution condition, whether the module is automatically executed or manually executed, in other words, whether the module requires determination and operation by the operator 70 is set. An input condition necessary for executing the processing and the output content output as a result of the processing are preset in each registered module. When the operator 70 connects a plurality of modules, the workflow manager 10 verifies the workflow based on whether an output condition of a connection source module satisfies an input condition of a connection destination module. If the output condition of the connection source module satisfies the input condition of the connection destination module, the workflow manager 10 performs connection between the modules. On the other hand, if the output condition of the connection source module does not satisfy the input condition of the connection destination module, the workflow manager 10 displays the error message.

The workflow is constructed by connecting registered modules. In addition, a new workflow can be created by reading and correcting the registered workflow.

Next, effects of the present embodiment will be described.

In the present embodiment, it is possible to shorten a treatment time by executing a module requesting an operation by the operator 70 and a module of the next process in parallel.

Specifically, during execution of step S106 of the positioning process P1, steps S201 to S207 of the contour creation process P2, S301 to S305 of the re-planning process P3, steps S401 to S403 of the patient QA process P4, and S501 of the irradiation process P5 can be executed in parallel. Further, during execution of step S208 of the contour creation process P2, steps S301 to S305 of the re-planning process P3, steps S401 to S403 of the patient QA process P4, and S501 of the irradiation process P5 can be executed in parallel. Furthermore, during execution of step S306 of the re-planning process P3, steps S401 to S403 of the patient QA process P4, and S501 of the irradiation process P5 can be executed in parallel.

Thus, it is possible to reduce the time required for the online adaptive treatment in online adaptive radiotherapy including a large number of implementation matters to be performed on the day.

Furthermore, in the present embodiment, the steps executed in each process are managed as modules divided for each element, and the workflow is constructed as a connection of the modules. This makes it possible to easily recognize modules that can be executed in parallel. In addition, the connection between the modules can be easily constructed and changed, and a flexible workflow according to the preference of a hospital or a doctor can be constructed. Furthermore, it is possible to construct a highly scalable workflow that can be updated in units of modules.

In addition, in the present embodiment, by displaying the progress status of the workflow using a workflow diagram expressed as the connection of the modules, it is possible to easily recognize a completion status of modules executed in parallel.

Note that the present invention is not limited to the above-described embodiments, and includes various modifications. The above-described embodiments have been described in detail in order to describe the present invention in an easy-to-understand manner, and are not necessarily limited to those having all described configurations.

For example, the workflow illustrated in FIG. 4 is an example, and the steps managed as modules may be further subdivided, and a plurality of steps may be managed by one module. The steps illustrated in FIG. 4 can be omitted, and an order of execution can be changed.

Further, the patient positioning system 11, the contour creation system 12, the re-planning system 13, and the patient QA system 14 may be the same system or may be a part of function of the workflow manager 10.

Further, some or all of the above-described configurations, functions, processing units, processing means, and the like may be realized by hardware, for example, by designing with an integrated circuit. Further, each of the above-described configurations, functions, and the like may be realized by software by a processor interpreting and executing a program for realizing each function. Information such as a program, a table, and a file for realizing each function can be stored in a recording device such as a memory, a hard disk, and an SSD, or a recording medium such as an IC card, an SD card, and a DVD.

Furthermore, control lines and information lines indicate what is considered to be necessary for the description, and do not necessarily indicate all the control lines and the information lines on a product. In practice, it may be considered that almost all the configurations are connected to each other.

REFERENCE SIGNS LIST 1 radiotherapy system
10 workflow manager
11 patient positioning system
12 contour creation system
13 re-planning system
14 patient QA system
20 imaging apparatus
21 imaging control system
30 irradiation nozzle
31 irradiation control system
40 rotating gantry
41 gantry control system
50 couch
51 couch control system
60 patient
61 target
70 operator

The invention claimed is:

1. A workflow management system that executes a plurality of processes executed to execute a radiotherapy according to a predetermined workflow, the workflow management system comprising:
a first CPU, configured to:
execute at least a first process and a second process of the plurality of processes, and
execute in parallel:
display, in the first process, a result of a first calculation based on a patient image captured during a treatment by an imaging apparatus that captures a predetermined region of a patient, and requests an input from an operator, and
execute, in the second process, a second calculation based on the patient image during the treatment.

2. The workflow management system according to claim 1, wherein the first CPU is further configured to execute the second calculation using the result of the first calculation.

3. The workflow management system according to claim 1, wherein the first CPU is further configured to determine whether to execute the first calculation again on a basis of the input from the operator.

4. The workflow management system according to claim 3, wherein the first CPU is further configured to discard the second calculation when determining to execute the first calculation again.

5. The workflow management system according to claim 1, further comprising:
a plurality of CPUs, including the first CPU, that execute the plurality of processes including processes different from each other; and
a management CPU configured to instruct one or more of the plurality of CPUs to execute a module.

6. The workflow management system according to claim 5, wherein the plurality of CPUs further includes a second CPU, and wherein the management CPU is further configured to:
receive a calculation result from the first CPU, and
transmit the calculation result to the second CPU different from the first CPU.

7. The workflow management system according to claim 5, wherein the first CPU is further configured to wait to execute the first process and the second process until receiving an instruction from the management CPU.

8. The workflow management system according to claim 5, wherein the plurality of CPUs are connected to create the predetermined workflow.

9. The workflow management system according to claim 8, wherein the first CPU is further configured to verify the predetermined workflow on a basis of an output condition of a connection source and an input condition of a connection destination.

10. The workflow management system according to claim 8, wherein the first CPU is further configured to:

display the predetermined workflow by displaying a connection state during an execution of the predetermined workflow, and display a progress status of the predetermined workflow.

11. A radiotherapy system comprising:

an imaging apparatus that images a predetermined region of a patient including a target;

a radiation irradiation device for irradiating the target with radiation; and a CPU configured to:

execute a plurality of processes to execute a radiotherapy according to a predetermined workflow, the plurality of processes including at least a first process and a second process, and execute in parallel:

display a result of a first calculation based on a patient image captured during a treatment by the imaging apparatus that captures a predetermined region of a patient, and request an input from an operator, and execute a second calculation based on the patient image during the treatment.

12. A workflow management method executed by one or more CPUs that execute a plurality of processes to execute a radiotherapy according to a predetermined workflow, wherein the plurality of processes includes at least a first process and a second process, the workflow management method comprising:

executing in parallel:

displaying, in the first process, a result of a first calculation based on a patient image captured during a treatment by an imaging apparatus that captures a predetermined region of a patient, and requesting an input from an operator; and executing, in the second process, a second calculation based on the patient image during the treatment.

13. A workflow management system that executes a plurality of processes to execute a radiotherapy according to a predetermined workflow, the workflow management system comprising:

a first CPU, configured to:

execute at least a first process and a second process of the plurality of processes, the first process including requesting an operator to perform a determination process of a calculation process and a result of the calculation process, execute, in the first process, a calculation process based on a patient image that captured a predetermined region of a patient before an irradiation, and execute, in the second process, a calculation process based on the result of the calculation process of the first process during an execution of the determination process.

14. The workflow management system according to claim 13, wherein the first CPU is further configured to determine, in the first process, whether to execute the calculation process based on the patient image again based on an input from the operator according to the determination process.

15. The workflow management system according to claim 14, wherein the first CPU is further configured to discard the calculation process of the second process when determining to execute the calculation process of the first process based on the patient image again.

16. The workflow management system according to claim 13, further comprising:

a plurality of CPUs, including the first CPU, that execute the plurality of processes including processes different from each other; and a management CPU configured to instruct one or more of the plurality of CPUs to execute a module.

17. The workflow management system according to claim 16, wherein the plurality of CPUs further includes a second CPU, and wherein the management CPU is further configured to:

receive a calculation result from the first CPU, and transmit the calculation result to the second CPU different from the first CPU.

18. The workflow management system according to claim 16, wherein the first CPU is further configured to wait to execute the first process and the second process until receiving an instruction from the management CPU.

19. The workflow management system according to claim 16, wherein the plurality of CPUs are connected to create the predetermined workflow.

* * * * *